United States Patent
Loomis

(10) Patent No.: US 7,118,550 B2
(45) Date of Patent: Oct. 10, 2006

(54) SIDE-DELIVERY SUPPOSITORY DISPENSER

(75) Inventor: Benjamin N. Loomis, Topton, PA (US)

(73) Assignee: B. Braun Medical, Bethlehem, PA (US)

( * ) Notice: Subject to any disclaimer, the term of this patent is extended or adjusted under 35 U.S.C. 154(b) by 443 days.

(21) Appl. No.: 10/616,761

(22) Filed: Jul. 10, 2003

(65) Prior Publication Data

US 2005/0010160 A1    Jan. 13, 2005

(51) Int. Cl.
A61M 25/00 (2006.01)
A61M 31/00 (2006.01)
B65D 83/04 (2006.01)

(52) U.S. Cl. .......................... 604/60; 604/11; 604/285

(58) Field of Classification Search ............ 604/11–18, 604/514–15, 57, 59–64, 208–210, 285–288, 604/82, 84, 125, 181, 187, 218, 225; 600/3, 600/6–8, 33–35
See application file for complete search history.

(56) References Cited

U.S. PATENT DOCUMENTS

| | | | | |
|---|---|---|---|---|
| 1,537,257 A | * | 5/1925 | Mizner | 604/13 |
| 1,691,981 A | * | 11/1928 | Mayol | 401/66 |
| 2,373,520 A | * | 4/1945 | Wallin | 604/210 |
| 2,409,656 A | * | 10/1946 | Austin | 604/210 |
| 2,616,422 A | | 11/1952 | Jones | |
| 2,718,299 A | * | 9/1955 | Atwater et al. | 206/537 |
| 2,824,667 A | * | 2/1958 | Barnett | 221/266 |
| 2,856,928 A | | 10/1958 | Zener | |
| 2,907,327 A | * | 10/1959 | White | 604/60 |
| 3,166,216 A | * | 1/1965 | Guarr | 221/289 |
| 3,276,626 A | * | 10/1966 | Stevens | 221/257 |
| 3,612,349 A | * | 10/1971 | Thomas | 221/4 |
| 3,831,605 A | | 8/1974 | Fournier | |
| 4,043,338 A | | 8/1977 | Homm et al. | |
| 4,174,048 A | * | 11/1979 | Volpe, Jr. | 221/267 |
| 4,361,150 A | | 11/1982 | Voss | |
| 4,474,308 A | * | 10/1984 | Bergeron | 221/24 |
| 4,592,740 A | * | 6/1986 | Mahruki | 604/15 |
| 4,636,202 A | | 1/1987 | Lowin et al. | |
| 4,700,692 A | * | 10/1987 | Baumgartner | 600/7 |
| 4,808,166 A | * | 2/1989 | Davidov | 604/114 |
| 4,900,303 A | * | 2/1990 | Lemelson | 604/514 |
| 4,990,136 A | | 2/1991 | Geria | |
| 5,002,540 A | | 3/1991 | Brodman et al. | |

(Continued)

OTHER PUBLICATIONS

Vagifem Tablets (Pharmacia & Upjohn), Physicians Desk Reference (PDR) vol. 57, 17 pages (2003).

Primary Examiner—Karin Reichle
(74) Attorney, Agent, or Firm—RatnerPrestia

(57) ABSTRACT

A dispenser for delivering a suppository within a body cavity. The dispenser has two main components: a barrel and a plunger. The barrel includes a head, a foot, and a body having a length and extending between the head and the foot. The barrel further defines an axial passage disposed along substantially the entire length of the body beginning at the foot and ending proximate the head, and includes a side aperture providing external access through the body of the barrel to the axial passage at the head of the barrel. The plunger includes a nose, a tail, and a frame extending between the nose and the tail. The plunger is sized to travel within the axial passage of the barrel between a relaxed position and a compressed position, in which a suppository is ejected from the side aperture, upon actuation.

19 Claims, 4 Drawing Sheets

U.S. PATENT DOCUMENTS

| | | |
|---|---|---|
| 5,213,566 A | 5/1993 | Weissenburger |
| 5,263,934 A * | 11/1993 | Haak ........................... 604/110 |
| 5,330,427 A | 7/1994 | Weissenburger |
| 5,342,394 A * | 8/1994 | Matsuno et al. ............. 606/213 |
| D353,999 S | 1/1995 | Hansen et al. |
| 5,380,295 A * | 1/1995 | Vacca ........................... 604/187 |
| 5,405,011 A * | 4/1995 | Haber et al. ................. 206/531 |
| 5,405,324 A * | 4/1995 | Wiegerinck ................... 604/60 |
| 5,501,664 A * | 3/1996 | Kaldany ...................... 604/57 |
| 5,507,807 A * | 4/1996 | Shippert ........................ 623/8 |
| 5,788,664 A | 8/1998 | Scalise |
| 5,860,946 A | 1/1999 | Hofstatter |
| 5,904,670 A | 5/1999 | Schreiner |
| 6,123,683 A | 9/2000 | Propp |
| 6,162,203 A * | 12/2000 | Haaga ......................... 604/272 |
| 6,213,663 B1 * | 4/2001 | Micaletti et al. ............. 401/176 |
| 6,258,070 B1 * | 7/2001 | Kaldany ...................... 604/264 |
| 6,572,527 B1 * | 6/2003 | Steele et al. ................... 600/7 |
| 6,786,883 B1 * | 9/2004 | Shippert ....................... 604/15 |
| 2002/0177582 A1 | 11/2002 | Maloney |
| 2003/0023189 A1 | 1/2003 | Kuo |

* cited by examiner

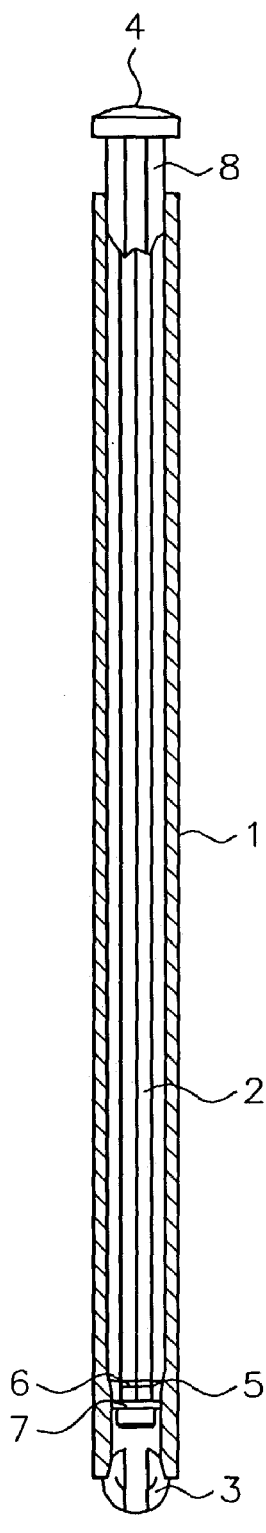
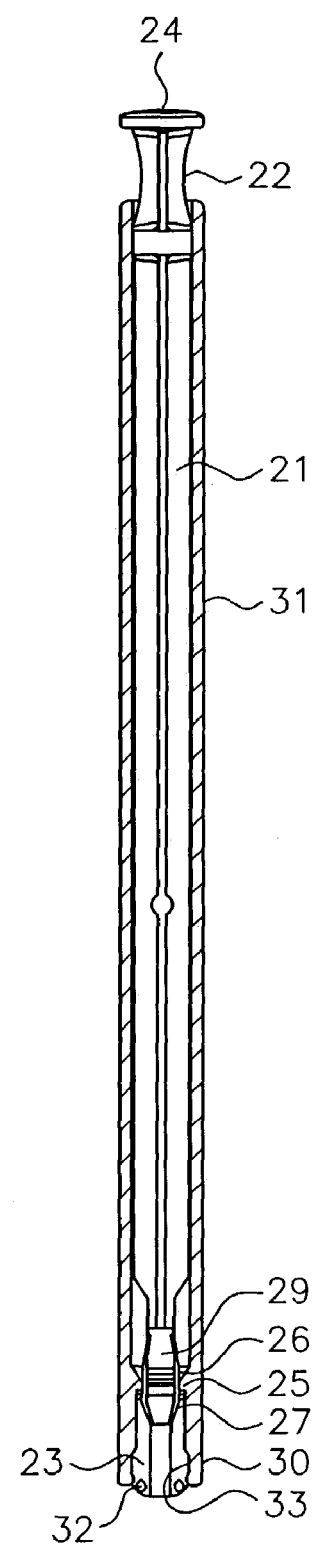
FIG. 1
(Prior Art)
FIG. 2
(Prior Art)

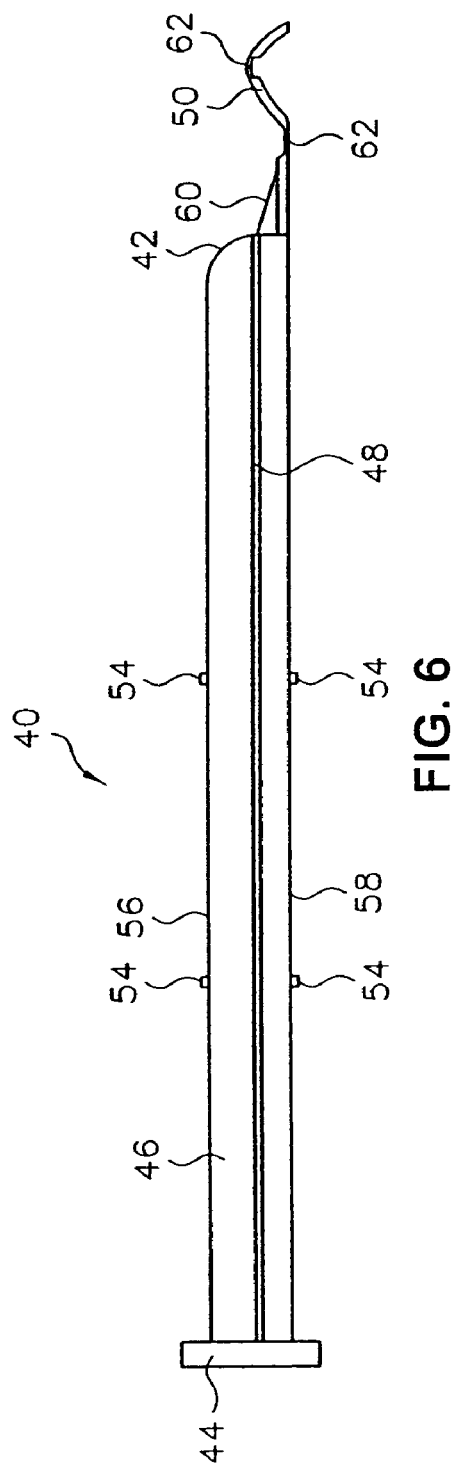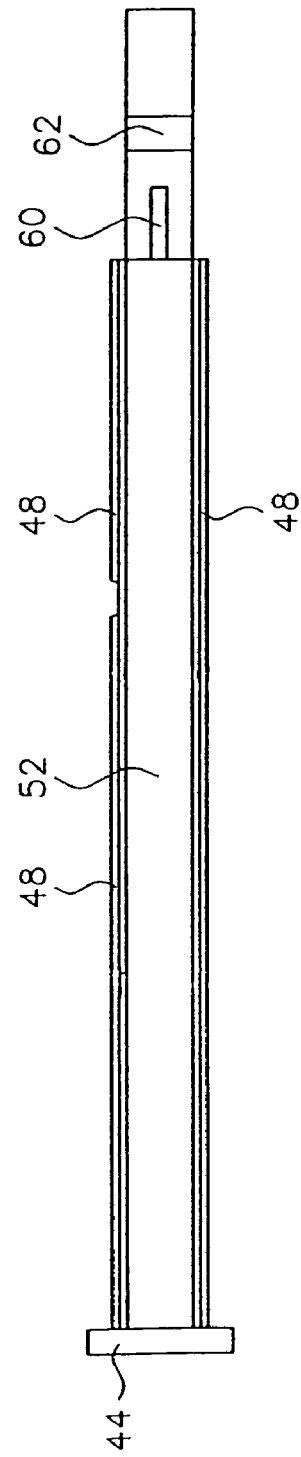

SIDE-DELIVERY SUPPOSITORY DISPENSER

FIELD OF THE INVENTION

The present invention relates generally to instruments for medication delivery and, more particularly, to a dispenser for delivering a suppository within a body cavity.

BACKGROUND OF THE INVENTION

In the health care industry, there exist various methods by which medication can be given to a patient. These methods may require inhalation, injection, or application of the medication to a body cavity. More specifically, some types of medications require gradual adsorption in the body of a patient, and thus a suppository (generally in the form of a tablet) is introduced within a particular body cavity in order to meet this need. It is well known practice to administer such suppositories by use of manual applicators, which provide safe, hygienic, and controlled delivery of the suppository. It is desired that these manual applicators dispense the tablet upon actuation by the patient and leave the tablet in the dispensed location while and after the applicator is removed. In addition, it is desired that the applicators do not cause irritation or pain to the user.

Most applicators are structured such that the suppository is placed in a tube while a plunger is manually advanced through the tube to push the suppository into the body cavity. U.S. Pat. No. 5,860,946 issued to Hofstätter discusses a typical applicator, illustrated in FIG. 1. Hofstätter also offers the improvement illustrated in FIG. 2.

FIG. 1 shows a plunger 2 having a quadratic cross section as inserted in a tubular housing 1. At an end of the housing 1, lips 3 are provided to support a suppository which may be expelled by the plunger when a button 4 at a projecting end of the plunger 2 is depressed by the user. At its expelling end, the plunger 2 has a circular cross section and is provided with axially spaced flanges 6 and 7. An inward shoulder 5 on the tubular housing 1 engages between the flanges 6 and 7 to fix the plunger 2 against unintentional axial movement. When the applicator is used, it is inserted in a body cavity, or where the suppository is going to be placed, and the button 4 is depressed. When the pressure is sufficient to overcome the resiliency of the flange 6, this flange 6 will be moved past the shoulder 5. The rear end of the plunger 2 has a part 8 with an enlarged cross section to maintain the plunger 2 running along the axis of the tubular housing 1.

FIG. 2 shows a sectional view of a tubular housing 31 with a plunger 22 as taught by Hofstätter. The tubular housing 31 has a first end adapted to receive a suppository between two tongues 30 and a second end through which the plunger 22 is inserted in the tubular housing 31. The plunger 22 has a first end, with a circular cross section and two axially spaced circumferential flanges 26, 27, and a second end projecting from the second end of the tubular housing 31. The first end of the tubular housing 31 has an inwardly extending shoulder 25 which engages between the flanges 26, 27. The first end of the plunger 22 is divided by radial slots into an uneven number of sectors 29. The plunger 22 has between its first end and a press button 24 at its second end angular spaced radial walls 21 abutting the inner wall of the tubular housing 31. Thus, the axial-spaced, disc-shaped walls 21 have a diameter corresponding to the inner diameter of the tube 31. A tablet (not shown) is held in the recesses 33 of the tongues 30. A pair of lips 23 with protrusions 32 prevent the tablet from exiting the tubular housing 31 in the axial direction.

The applicators discussed and taught by Hofstätter are typical of conventional applicators. Such applicators have a tube with a tapered end through which the suppository is ejected. This tapered end is often the cause of irritation and pain to the patient. Furthermore, conventional applicators do not offer a feature by which a patient can determine whether or not the suppository has been fully dispensed, often resulting in improper placement of the suppository within the body cavity.

To overcome these shortcomings, a new suppository dispenser design is provided. An object of the present invention is to provide an improved suppository dispenser aimed at improving patient comfort. A related object is to dispense the suppository from the side of the dispenser, allowing the dispenser to have a fully rounded tip. Another object is to provide a physical sensation when the plunger has been fully depressed in order to indicate that a suppository has been fully ejected.

A further object of the present invention is to provide a dispenser that securely holds a tablet during packaging, transport, and insertion. A still further object is to provide a device that dispenses the tablet upon actuation by the patient. A device that leaves the tablet in its dispensed location, while and after the device is removed, is another object.

SUMMARY OF THE INVENTION

To achieve these and other objects, and in view of its purposes, the present invention provides a dispenser for delivering a suppository within a body cavity. The dispenser has two, main components: a barrel and a plunger. The barrel includes a head, a foot, and a body having a length and extending between the head and the foot. The barrel further defines an axial passage disposed along substantially the entire length of the body beginning at the foot and ending proximate the head, and includes a side aperture providing external access through the body of the barrel to the axial passage at the head of the barrel. The plunger includes a nose, a tall, and a frame extending between the nose and the tail. The plunger is sized to travel within the axial passage of the barrel between a relaxed position and a compressed position, in which a suppository is ejectable from the side aperture, upon actuation.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. According to the present invention included in the drawing are the following figures:

FIG. 1 is a sectional view of an insertion instrument according to the known art;

FIG. 2 is a sectional view of another insertion instrument according to the known art;

FIG. 6 is a side view of the plunger of the dispenser according to the present invention;

FIG. 7 is a top view of the plunger of the dispenser according to the present invention;

DETAILED DESCRIPTION OF THE INVENTION

Figure 3:
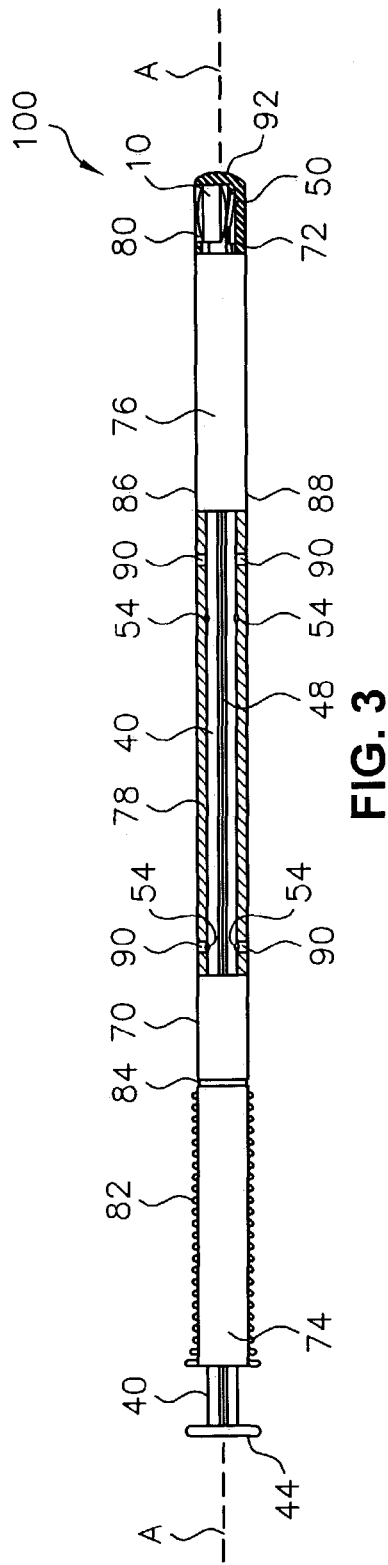
FIG. 3 is a partial cross-sectional side view of the dispenser according to the present invention, as loaded with a tablet, with the plunger in a relaxed position.

Referring now to the drawings, in which like reference numbers refer to like elements throughout the various figures that comprise the drawings, FIG. 3 is a partial cross-sectional side view of the dispenser 100 according to the present invention, as loaded with a tablet 10, with the plunger 40 as yet undepressed within the barrel 70. The dispenser 100 has two, main components: the barrel 70 and the plunger 40. Both the barrel 70 and the plunger 40 are preferably made of plastic material, most preferably plastics from the polyolefin family. Other flexible plastics could be used.

As illustrated in FIG. 3, the barrel 70 includes a head 72, a foot 74, and a body 76 having a length and extending between the head 72 and the foot 74. The barrel 70 further defines an axial passage 78 disposed along substantially the entire length of the body 76 beginning at the foot 74 and ending proximate the head 72, and includes a side aperture 80 providing external access through the body 76 of the barrel 70 to the axial passage 78 at the head 72 of the barrel 70.

As best illustrated in FIG. 6, the plunger 40 includes a nose 42, a tail 44, and a frame 46 extending between the nose 42 and the tail 44. The plunger 40 is sized to travel within the axial passage 78 of the barrel 70 between a relaxed position and a compressed position, in which a suppository such as the tablet 10 is ejected from the side aperture 80, upon actuation. A folding protrusion 50 extends from the nose 42 of the plunger 40 that functions to push the tablet 10 out through the side aperture 80 upon actuation of the plunger 40.

In an exemplary embodiment, the barrel 70 is about 130.5 mm (5.13& inches) long, 5.7 mm (0.225 inches) in height, and 8.6 mm (0.340 inches) wide. Disposed along approximately (although not necessarily) the first 30 mm (1.2 inches) of the length of the barrel 70, beginning at the foot 74 of the barrel 70, are a series of ribs 82. The ribs 82 are disposed along the exterior of the barrel 70 to provide texture for the user to securely grip the barrel 70 during manipulation of the dispenser 100.

Following the ribs 82, approximately 31 mm (1.22 inches) from the foot 74 of the barrel 70, a depth indicator 84 is provided on the external surface of the barrel 70. The depth indicator 84 is a groove or recess around the entire circumference of the barrel 70 about 1 mm (0.04 inches) wide. The depth indicator 84 informs the user how far the head 72 of the barrel 70 has been inserted into a body cavity and, hence, the position of the tablet 10 within the body cavity.

Each of the top 86 and the bottom 88 of the barrel 70 have two pairs of holes 90. The first pair of holes 90 is located about 46 mm (1.81 inches) from the foot 74 of the barrel 70. The two pair of holes 90 are separated by about 42 mm (1.65 inches). Thus, a total of eight holes 90 are provided in the body 76 of the barrel 70 of the dispenser 100.

The head 72 of the barrel 70 presents a solid, smooth, continuous, rounded surface 92 to the patient. There are no breaks, fingers, protrusions, separations, or other discontinuities in the rounded surface 92. Thus, the rounded surface 92 allows the dispenser 100 to be inserted into the body cavity of the patient with comfort—avoiding irritation, pain, and the risk of "catching" on the patient.

Figure 9:
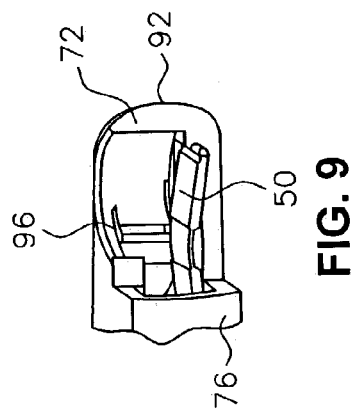
FIG. 9 is a partial cross-sectional view of the barrel head highlighting the gripper fingers.

Inside the head 72 of the barrel 70 are disposed one or more profiled protrusions or gripping fingers 96 (best shown in FIG. 9) which help to secure the tablet 10 in the barrel 70. Thus, the dispenser 100 holds the tablet 10 securely during packaging, transportation, and insertion by the user of the dispenser 100 inside a body cavity.

Figure 4:
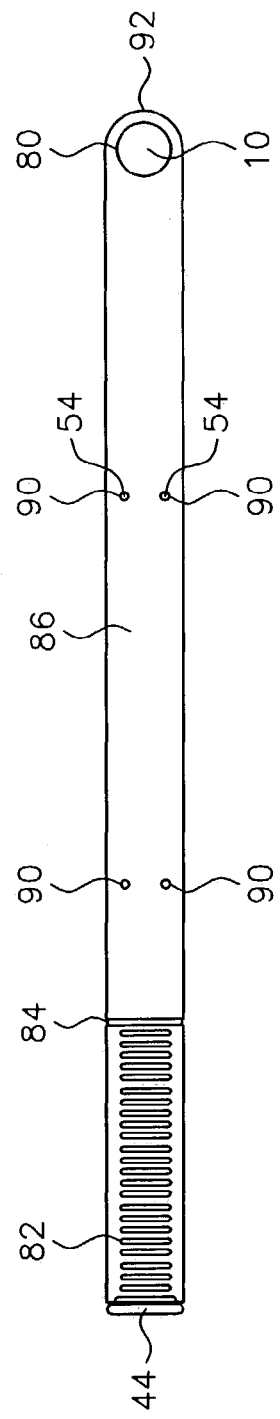
FIG. 4 is a top view of the dispenser according to the present invention with the plunger in a compressed position in the barrel.

The side aperture 80 is disposed in the head 72 of the barrel 70, as best illustrated in FIG. 4. Typically, the side aperture 80 is circular in shape, although other shapes are possible to meet the requirements of a particular application. For example, if the tablet 10 is oval rather than round, the side aperture 80 may be oval. In an exemplary embodiment, the side aperture is a circle having a diameter of about 6 mm (0.24 inches). The side aperture 80 engages the axial passage 78 of the barrel 70.

The top 86 of the barrel 70 optionally has a guide 94 disposed on its inner surface. If included, the guide 94 is disposed in the axial passage 78 and runs the length of the barrel 70 from the head 72 to the foot 74. An end of the guide 94 is visible in FIGS. 8A, 8B, and 8C. Guide 94 is not required for the dispenser 100 to function.

Turning to the plunger 40, as best illustrated in FIG. 6, the dimensions of the plunger are selected to correspond to those of the barrel 70. In the exemplary embodiment illustrated, the frame 46 of the plunger 40 has a length between the tail 44 and the nose 42 of about 121 mm (4.76 inches). The plunger 40 is about 4 mm (0.16 inches) tall and about 6.5 mm (0.256 inches) wide. The tail 44 of the plunger 40 defines a round button about 1 mm thick (0.04 inches) and 8.5 mm (0.033 inches) in diameter. The button of the tail 44 allows the user easily to push the plunger 40 inward relative to the barrel 70, causing the plunger 40 to slide along the axial passage 78 of the barrel 70.

The plunger 40 has a pair of side rails 48 disposed along the length of the frame 46. The side rails 48 contact the inside walls of the body 76 of the barrel 70 as the plunger 40 traverses the axial passage 78, as necessary, to maintain the plunger 40 running along the axis A of the barrel 70. The top 56 of the plunger 40 defines a track 52 which receives the guide 94 of the barrel 70 when the plunger 40 is inserted in the axial passage 78 of the barrel 70. The combination of the guide 94 and the track 52 causes the plunger 40 to slide along the axial passage 78 of the barrel 70.

The guide 94 of the barrel 70 also assures that the user inserts the plunger 40 into the axial passage 78 with the plunger 40 oriented correctly relative to the barrel 70. When the plunger 40 and the barrel 70 are properly aligned, the guide 94 of the barrel 70 engages the track 52 and the plunger 40 slides smoothly into the axial passage 78. When the plunger 40 and the barrel 70 are improperly aligned, however, with the plunger 40 upside down relative to the barrel 70, the guide 94 of the barrel 70 causes the plunger 40 to abut the end of the barrel 70 defined by the foot 74, preventing the plunger 40 from entering the axial passage 78. The user then simply rotates the plunger 40 approximately 180° relative to the barrel 70 to obtain proper alignment between the plunger 40 and the barrel 70.

Each of the top 56 and the bottom 58 of the plunger 40 have two pairs of flexible locator tabs 54. The first pair of locator tabs 54 is placed about 53 mm (2.09 inches) from the tail 44 of the plunger 40. The two pairs of locator tabs 54 are separated by about 36 mm (1.42 inches). Thus, a total of eight locator tabs 54 are provided on the frame 46 of the plunger 40 of the dispenser 100.

The locator tabs 54 of the plunger 40 engage the holes 90 of the barrel 70. Specifically, when the plunger 40 is disposed in the axial passage 78 of the barrel 70 in a first, unactuated or relaxed position (as shown in FIG. 3), the first pair (i.e., closest to the tail 44) of locator tabs 54 on both the top 56 and the bottom 58 of the plunger 40 engage the corresponding first pair (i.e., closest to the foot 74) of holes 90 on both the top 86 and the bottom 88 of the barrel 70. The flexible locator tabs 54 slide along the axial passageway 78 until they reach the holes 90, at which point the locator tabs 54 spring into the holes 90 and hold the plunger 40 in a relatively fixed position with respect to the barrel 70. This spring action also indicates to the user that the dispenser 100 is in its unactuated or "loaded" position. In this position, shown in FIG. 3, the tail 44 of the plunger 40 extends beyond the foot 74 of the barrel 70 by a distance of about 8.86 mm (0.349 inches).

When the user desires to actuate the dispenser 100 from the loaded position and eject a tablet 10, a force is applied (along the direction F in FIG. 8B) to push the plunger 40 further into the barrel 70. The force applied is sufficient to cause the flexible locator tabs 54 to exit the first pair of holes 90 in the barrel 70. The plunger 40 then continues to slide along the axial passage 78 until the second pair (i.e., closest to the nose 42) of locator tabs 54 on both the top 56 and the bottom 58 of the plunger 40 engage the corresponding second pair (i.e., closest to the head 72) of holes 90 on both the top 86 and the bottom 88 of the barrel 70. At this point, shown in FIGS. 4 and 5, the locator tabs 54 spring into the holes 90 and hold the plunger 40 in a relatively fixed position with respect to the barrel 70. This spring action also indicates to the user that the dispenser 100 is in its compressed or fully actuated or "ejected" position. In this position, the tail 44 of the plunger 40 is substantially flush against the foot 74 of the barrel 70. Thus, the locator tabs 54 and holes 90 combine to provide to the user a physical indication of the position of the plunger 40 relative to the barrel 70.

As shown in FIGS. 6 and 7, the folding protrusion 50 extends from the nose of the plunger 40. The folding protrusion 50 physically pushes the tablet 10 through the side aperture 80 and out of the barrel 70—as described in more detail below. In its fully extended state, the folding protrusion 50 is about 16 mm (0.63 inches) long. A wedge-shaped reinforcement 60 is provided on the folding protrusion 50 in the portion of the folding protrusion 50 that need not fold. Two reduced material sections constitute hinges 62 which facilitate folding of the folding protrusion 50.

Figure 8A:
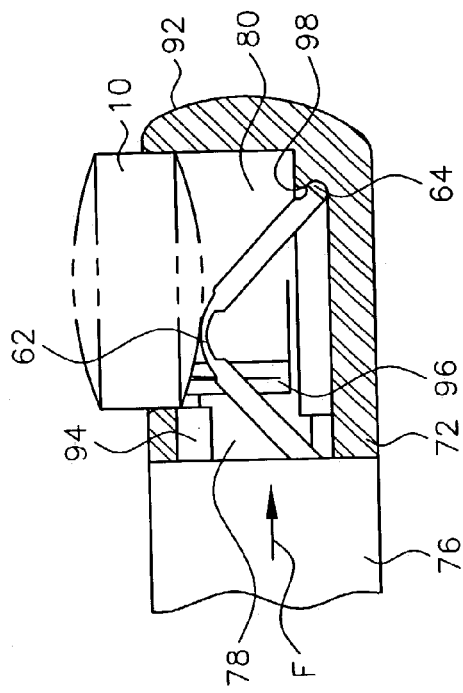
FIG. 8A is a side view of the dispenser according to the present invention, as loaded with a tablet, with a partial cross-section showing the barrel head.

When the dispenser 100 is in its unactuated or "loaded" position, as shown in FIG. 3, the tablet 10 is contained within the side aperture 80 of the barrel 70 with the help of gripping fingers 96. The tablet 10 rests on top of the fully extended folding protrusion 50. The tip 64 of the folding protrusion 50 just abuts a shoulder 98 on the head 72 of the barrel 70. The relationships among the tablet 10, the folding protrusion 50 of the plunger 40, and the barrel 70 in the loaded position are illustrated in FIG. 8A.

Figure 8B:
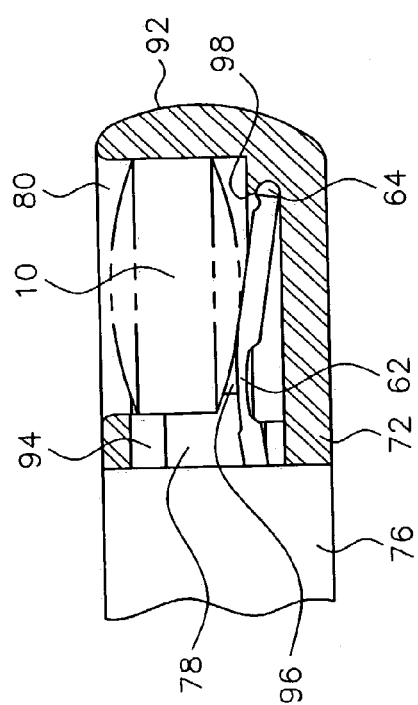
FIG. 8B is a side view of the dispenser according to the present invention, illustrating the tablet partially ejected, with a partial cross-section showing the barrel head.

When the user desires to actuate the dispenser 100, the user exerts a force in the direction of arrow F as shown in FIG. 8B. This force causes the folding protrusion 50 to fold at its hinges 62, given that the shoulder 98 of the barrel 70 prevents the folding protrusion 50 from moving forward in the head 72 of the barrel 70 in the axially or longitudinal direction. As the folding protrusion 50 begins to fold, the folding protrusion 50 pushes the tablet 10 upward in the side aperture 80 in a direction perpendicular to the axially or longitudinal direction. In intermediate actuation, the dispenser 100 is put in a mid-ejection state illustrated in FIG. 8B: the tablet 10 is pushed partially out of the gripping fingers 96 and extends partially out of the side aperture 80.

Figure 5:
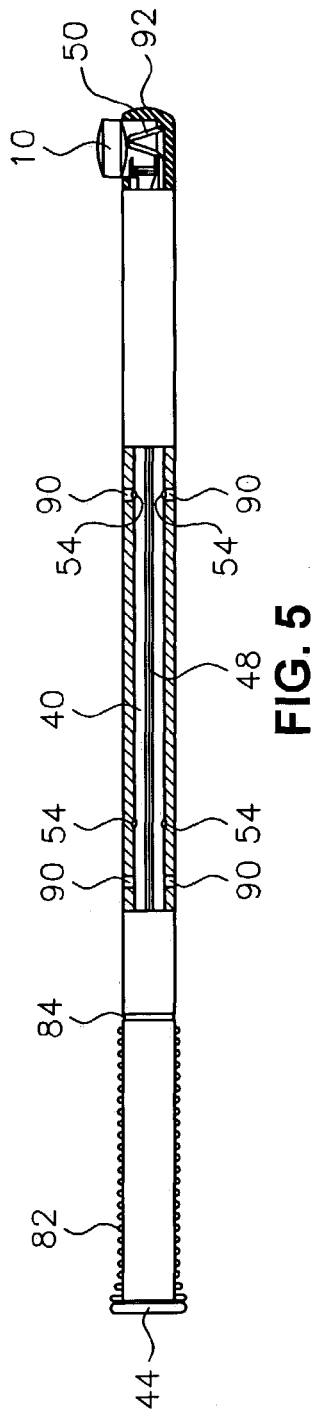
FIG. 5 is a partial cross-sectional side view of the dispenser according to the present invention with the plunger in the compressed position in the barrel and a tablet just ejected from the dispenser.
Figure 8C:
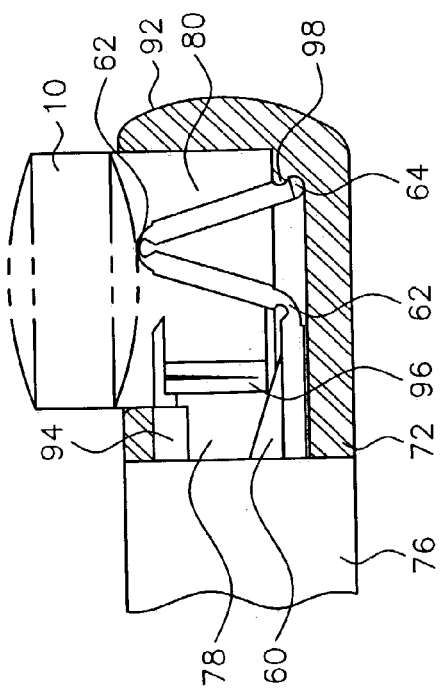
FIG. 8C is a side view of the dispenser according to the present invention, illustrating the tablet fully ejected, with a partial cross-section showing the barrel head.

Upon continued exertion of force by the user, the dispenser achieves the fully actuated, ejected state illustrated in FIGS. 4, 5, and 8C. The folding projection 50 is fully compressed, causing the folding projection 50 to bend completely about its hinges 62. Such bending raises the folding projection 50 to its maximum height, pushing the tablet 10 completely out of the gripping fingers 96 and consequently out of the side aperture 80.

Once the user has positioned the dispenser 100 properly inside the body cavity, the user actuates the dispenser 100 by pushing the plunger 40 into the axial passage 78 while holding the barrel 70 via the ribs 82. Such actuation causes the dispenser 100 to dispense the tablet 10 into the body cavity. The user then withdraws the dispenser 100 from the body cavity. Such withdrawal leaves the tablet 10 in its dispensed location.

Although illustrated and described above with reference to certain specific embodiments, the present invention is nevertheless not intended to be limited to the details shown. Rather, various modifications may be made in the details within the scope and range of equivalents of the claims and without departing from the spirit of the invention.

What is claimed is:

1. A dispenser for delivering a suppository within a body cavity, the dispenser comprising:
    a barrel including a head, a foot, and a body having a length and extending between the head and the foot, the barrel further (a) defining an axial passage disposed along substantially the entire length of the body beginning at the foot and ending proximate the head, and (b) including a side aperture providing external access through the body of the barrel to the axial passage at the head of the barrel; and
    a plunger inserted in the axial passage and including a nose, a tail, and a frame extending between the nose and the tail and having a length sized to travel within the axial passage of the barrel between a relaxed position and a compressed position, and wherein the nose has a resilient folding protrusion extending therefrom for pushing the suppository through the side aperture as it folds upon travel of the plunger from its relaxed position toward its compressed position.

2. The dispenser according to claim 1, wherein the barrel further includes one or more gripping fingers disposed in the head to secure the suppository within the side aperture.

3. The dispenser according to claim 1, wherein the folding protrusion of the plunger has at least one hinge facilitating bending of the folding protrusion.

4. The dispenser according to claim 1, wherein the folding protrusion of the plunger has a tip and the head of the barrel has a shoulder, the tip abutting the shoulder and preventing movement of the folding protrusion in a first direction, thereby causing the folding protrusion to bend.

5. The dispenser according to claim 1, wherein the barrel further includes a depth indicator on its external surface.

6. The dispenser according to claim 1, wherein the barrel further includes a plurality of holes in its body and the plunger further includes a corresponding number of resilient locator tabs on the frame, the locator tabs engaging the holes to provide a physical indication of the position of the plunger relative to the barrel.

7. The dispenser according to claim 1, wherein the barrel further includes one or more ribs disposed along the exterior surface of the barrel to provide texture facilitating a secure gripping of the barrel.

8. The dispenser according to claim 1, wherein the barrel further includes a guide disposed on an inner surface of its body and the plunger further includes a corresponding track, the track receiving the guide when the plunger is inserted in the axial passage of the barrel.

9. The dispenser according to claim 1, wherein the head of the barrel presents a solid, smooth, continuous, rounded surface.

10. The dispenser according to claim 1, wherein the plunger further includes side rails disposed along the length of the frame, the side rails contacting inside walls of the body of the barrel as the plunger traverses the axial passage of the barrel, as necessary, to maintain the plunger running along the axis of the barrel.

11. A dispenser for delivering a suppository within a body cavity, the dispenser comprising:
 a barrel including a foot, a head having a shoulder and presenting a solid, smooth, continuous, rounded surface, and a body having a length and extending between the head and the foot, the barrel further (a) defining an axial passage disposed along substantially the entire length of the body beginning at the foot and ending proximate the head, and (b) including a side aperture providing external access through the body of the barrel to the axial passage at the head of the barrel; and
 a plunger inserted in the axial passage including:
  (a) a nose and a resilient folding protrusion extending from the nose, the folding protrusion having at least one hinge facilitating bending of the folding protrusion and a tip abutting the shoulder of the head of the barrel and preventing movement of the folding protrusion in a first direction parallel to the axial passage, thereby causing the folding protrusion to bend,
  (b) a tail adapted to receive force applied by a user to the plunger, and
  (c) a frame extending between the nose and the tail and having a length sized to travel within the axial passage of the barrel between a relaxed position and a compressed position, wherein the suppository is pushed through the side aperture by said protrusion as the plunger travels from its relaxed position toward its compressed position.

12. The dispenser according to claim 11, wherein the barrel further includes one or more gripping fingers disposed in the head to secure the suppository within the side aperture.

13. The dispenser according to claim 11, wherein the barrel further includes a depth indicator on its external surface.

14. The dispenser according to claim 11, wherein the barrel further includes a plurality of holes in its body and the plunger further includes a corresponding number of resilient locator tabs on the frame, the locator tabs engaging the holes to provide a physical indication of the position of the plunger relative to the barrel.

15. The dispenser according to claim 11, wherein the barrel further includes one or more ribs disposed along the exterior surface of the barrel to provide texture facilitating a secure gripping of the barrel.

16. The dispenser according to claim 11, wherein the barrel further includes a guide disposed on an inner surface of its body and the plunger further includes a corresponding track, the track receiving the guide when the plunger is inserted in the axial passage of the barrel.

17. The dispenser according to claim 11, wherein the plunger further includes side rails disposed along the length of the frame, the side rails contacting inside walls of the body of the barrel as the plunger traverses the axial passage of the barrel, as necessary, to maintain the plunger running along the axis of the barrel.

18. A dispenser for delivering a suppository within a body cavity, the dispenser comprising:
 a barrel including:
  (a) a foot,
  (b) a head having a shoulder and one or more gripping fingers for securing a suppository within the side aperture and presenting a solid, smooth, continuous, rounded surface, and
  (c) a body having a length and a plurality of holes and extending between the head and the foot, the barrel further (i) defining an axial passage disposed along substantially the entire length of the body beginning at the foot and ending proximate the head, and (ii) including a side aperture providing external access through the body of the barrel to the axial passage at the head of the barrel; and
 a plunger inserted in the axial passage including:
  (a) a nose and a resilient folding protrusion extending from the nose, the folding protrusion having at least one hinge facilitating bending of the folding protrusion and a tip abutting the shoulder of the head of the barrel and preventing movement of the folding protrusion in a first direction parallel to the axial passage, thereby causing the folding protrusion to bend,
  (b) a tail, and
  (c) a frame extending between the nose and the tail and having a length sized to travel within the axial passage of the barrel between a relaxed position and a compressed position, wherein the suppository is pushed through the side aperture by said protrusion as the plunger travels from its relaxed position toward its compressed position the frame further having a number of resilient locator tabs engaging the plurality of holes in the body of the barrel to provide a physical indication of the position of the plunger relative to the barrel.

19. The dispenser according to claim 18, wherein the barrel further includes a guide disposed on an inner surface of its body and the plunger further includes a corresponding track, the track receiving the guide when the plunger is inserted in the axial passage of the barrel.

* * * * *